(12) United States Patent
Lenges et al.

(10) Patent No.: US 7,439,354 B2
(45) Date of Patent: Oct. 21, 2008

(54) PROCESS FOR PREPARING AMIDE ACETALS

(75) Inventors: Christian Peter Lenges, Wilmington, DE (US); Josef Huybrechts, Turnhout (BE); Douglas J. Adelman, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 594 days.

(21) Appl. No.: 11/002,747

(22) Filed: Dec. 2, 2004

(65) Prior Publication Data

US 2005/0131164 A1  Jun. 16, 2005

Related U.S. Application Data

(60) Provisional application No. 60/529,268, filed on Dec. 11, 2003.

(51) Int. Cl.
 *C07D 491/04* (2006.01)
(52) U.S. Cl. ...................................... 540/468
(58) Field of Classification Search ................ 540/468
 See application file for complete search history.

(56) References Cited

U.S. PATENT DOCUMENTS

| 4,652,655 A | 3/1987 | Goel et al. |
| 4,683,077 A | 7/1987 | Goel |
| 4,721,767 A | 1/1988 | Goel |

FOREIGN PATENT DOCUMENTS

| DE | 3235933 | 3/1984 |
| EP | 0154254 A | 9/1985 |
| EP | 171811 A2 | 2/1986 |
| EP | 0279017 A2 | 8/1988 |
| WO | WO 2004/090056 A1 | 10/2004 |

OTHER PUBLICATIONS

Lewis, Terry W., 5-Perfluoralkyl Bicyclic Amide Acetals, Journal of Flourine Chemistry, 21 (1982) pp. 359-374.
Thierfelder et al., Preparation of Forms from Vegetable Oil Derivatives, Journal of American Oil Chemists' Society, 39, (1962) pp. 215-215.
Research Disclosure No. 427054, Oct. 11, 1999, Emsworth, GB, Anonymous: Low Viscosity Bicyclic Amide Acetal Compounds used as blocked Hydroxyl-Containing Compounds in Coating, Which provide a Long Pot Life and a Fast Drying Time. XP002319579.
The International Search Report and Written Opinion of the International Searching Authority, Application No. PCT/US2004/041709, Mailed: Apr. 27, 2005.

*Primary Examiner*—Kamal A Saeed
(74) *Attorney, Agent, or Firm*—Sudhir G. Desbmukh

(57) ABSTRACT

A process for preparing amide acetals represented in Formula I comprising dehydrating a reactant mixture comprising reactants selected from a group consisting of N-acyl dialkanol amines, O-acyl dialkanol amines and mixtures thereof

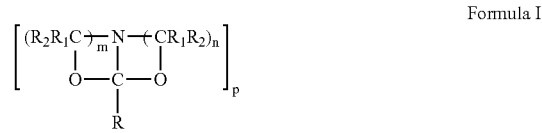

Formula I wherein
 n and m are independently 2 or 3; p is 1, 2 or 3; $R_1$ and $R_2$ can be the same or different and are each independently hydrogen, a linear or branched alkyl, cycloalkyl or aryl group with 1-20 C atoms; R represents hydrogen, a branched or linear alkyl, cycloalkyl, aryl or an alkenyl group with 1-20 C-atoms, each may have one or more substituents.

9 Claims, No Drawings

PROCESS FOR PREPARING AMIDE ACETALS

CROSS-REFERENCE TO RELATED APPLICATIONS

This application claims the benefit of U.S. Provisional Application Ser. No. 60/529,268 filed on Dec. 11, 2003, which is hereby incorporated by references in its entirely.

BACKGROUND OF THE INVENTION

The invention relates to a process for preparing bicyclic amide acetals from N-acyl dialkanol amines and/or O-acyl dialkanol amines. The bicyclic amide acetals can be used in coating compositions and crosslinked by hydrolyzing the amide acetal groups, and subsequently reacting the hydroxyl groups or amine groups that are formed with crosslinking agents.

DESCRIPTION OF THE RELATED ART

The synthesis of bicyclic amide acetals is known, e.g. by the reaction of dialkanol amines, such as diethanol amine with organic nitriles. U.S. Pat. No. 4,652,655 describes a process for preparation of bicyclic amide acetals by the reaction of organic nitriles with dialkanol amines wherein the reaction temperature is maintained below about 140° C. and the bicyclic amide acetal is removed from the reaction mixtures by extraction in a hydrocarbon solvent. European Patent application EP 171 811 describes a process for preparing bicyclic amide acetals by reacting diethanolamine and an alkyl nitrile in the presence of an alkali metal or an alkaline earth metal catalyst in a temperature range of 80° C. to 120° C. Ammonia is formed as a by-product in this reaction and needs to be removed, e.g. by purging with an inert gas.

In DE 32 35 933, bicyclic orthoester amides (bicyclic amide acetals) are described which are prepared by heating N-acyidialkanolamine-bis-alkyl carbonates in the presence of a catalyst, such as, sodium hydroxide followed by distillation of the reaction mixture.

Further, the preparation of 5-perfluoro-4,6-dioxa-1-azabicyclo(3.3.0)octanes is described by acid catalyzed dehydration of perflouroalkylamide-diols, wherein the electron withdrawing nature of the perflouroalkyl group enhances the electrophilicity of the amide carbonyl (Journal of Fluorine Chemistry, 21, 1982, 359-364).

Bicyclic amide acetals have been used for the production of polymers by reacting the bicyclic amide acetals with polyisocyanates at a temperature from about ambient temperature up to about 200° C. as disclosed in U.S. Pat. No. 4,721,767. These polymeric products can be used in applications, such as, reaction injection molding (RIM), in adhesives and coatings or as intermediates for life science products.

There is a need to provide an improved general process for making bicyclic amide acetals starting from simple commercially available reagents with improved conversion to the bicyclic amide acetal, and the formation of environmentally benign by-products such as water which results in a reduced environmental footprint and in the avoidance of waste streams. There is also a need to provide a process for the preparation of bicyclic amide acetals with low inherent color or color forming by-products.

SUMMARY OF THE INVENTION

The invention relates to a new process for preparing bicyclic amide acetals of the following formula I in a direct dehydration of a reactant mixture comprising N-acyl dialkanol amines and/or O-acyl dialkanol amines

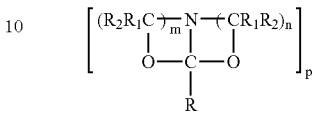

Formula I wherein
n and m are independently 2 or 3;
p is 1, 2 or 3;
$R_1$ and $R_2$ can be the same or different and are each independently hydrogen, a linear or branched alkyl, cycloalkyl or aryl group with 1-20 C atoms;
R represents hydrogen, a branched or linear alkyl, cycloalkyl, aryl or an alkenyl group with 1-20 C-atoms, each may have one or more substituents.

Preferably n is 2, and R is an alkyl, aryl or cycloalkyl group up to 20 C atoms.

DETAILED DESCRIPTION OF THE INVENTION

The reactant mixture comprising N-acyl dialkanol amines and/or O-acyl dialkanol amines used in this invention to prepare the bicyclic amide acetals can be provided by following one of the following different strategies:

A) The reactant mixture comprising N-acyl dialkanol amines and/or O-acyl dialkanol amines is formed by reacting at least one carboxylic acid and/or carboxylic acid ester and/or carboxylic acid anhydride and at least one dialkanol amine, optionally in the presence of a catalyst. Optionally, this process can be combined directly with the final dehydration process of the invention to form the bicyclic amide acetals.

B) Certain N-acyl dialkanol amines are commercially available or can be prepared using methods known in the art (see for example J. of the American Oil Chemists' Society (1962), 39, 213-15). Certain N-acyl dialkanol amines used as reactants can be prepared by reacting carboxylic amides and at least two equivalents of an epoxide, optionally in the presence of a catalyst. Compounds such as N-acyl alkanol amines and/or oxazolines are potential intermediates in this process and are within the scope of this invention.

Surprisingly, it has been found that bicyclic amide acetals can be prepared in a direct dehydration reaction of a mixture comprising N-acyl dialkanol amines and/or O-acyl dialkanol amines to form the bicyclic amide acetals and water as by-product. The use of a catalyst in this transformation is optional.

The process for preparing the bicyclic amide acetals of this invention can include any of the strategies A and/or B followed by a dehydration reaction to form the desired bicyclic amide acetals. These reactions can be separated into different process steps or carried out in one process step.

Based on strategy A, the bicyclic amide acetals of formula I are prepared according to the invention by reaction of carboxylic acids and/or carboxylic acid esters and/or carboxylic acid anhydrides with dialkanol amines. For example, the carboxylic acids which may be used are saturated or unsaturated carboxylic acids with at least one acid group, preferably one or two acid groups, and with 4 to 54 carbon atoms. Examples of suitable monocarboxylic acids are formic acid, acetic acid, propionic acid, butyric acid, isobutyric acid, pivalic acid, valeric acid, caproic acid, lauric acid, stearic acid, isononanoic acid, oleic acid, acrylic acid, methacrylic acid, crotonic acid and benzoic acid. Examples of suitable di- or tricarboxylic acids are maleic acid, phthalic acid, isophthalic acid, trimellitic acid, dodecanedicarboxylic acid, norbonane dicarboxylic acid, tetrahydrophthalic acid, hexahydrophthalic acid, methylhexahydrophthalic acid, cyclohexane-1,2- and -1,4-dicarboxylic acid, sebacic acid, and adipic acid.

Alternatively, the carboxylic acid esters of the carboxylic acids mentioned above can be used. Examples are carboxylic acid esters or carboxylic acid half esters of the carboxylic acids mentioned above with linear or branched alcohols with 1-20 C-atoms in the molecule. Preferably, methyl, ethyl, isopropyl, n-butyl, isobutyl alcohol esters are used. Alternatively, the carboxylic acid anhydrides of the carboxylic acids mentioned above can be used; these anhydrides can be based on monocarboxylic acids or dicarboxylic acids, which may form intramolecular anhydrides. Examples are acetic acid anhydride, caproic acid anhydride, succinic anhydride, and lauric acid anhydride.

The dialkanol amines useful in the process of this invention include substituted and unsubstituted dialkanol amines having the general formula

$HO(CR_1R_2)_m NH(CR_1R_2)_n OH$ wherein $R_1$, $R_2$, n and m have the meaning as defined above. Preferably, m and n are 2 and $R_1$ and $R_2$ can be the same or different and are each independently represented by hydrogen and a linear or branched alkyl group with 1-10 carbon atoms. Most preferred dialkanol amines are diethanol amine, di-n-propanol amine, and diisopropanol amine. These dialkanol amines are commercially available or can be prepared in an additional reaction step.

Dialkanol amines with n and m equal to 2 can also be prepared in a reaction of an alkanol amine with an oxirane. The oxiranes useful in this invention can be substituted with linear or branched alkyl, cycloalkyl or aryl groups; oxiranes based on glycidyl ethers are also useful compounds. Typical oxiranes include ethyleneoxide, propyleneoxide, butyleneoxide, phenyl glycidyl ether, and butylglycidyl ether. Typical alkanol amines are ethanolamine, 2-amino-propanol, and 1-amino-2-propanol.

The process of this invention, based on strategy A, is based on the reaction of the carboxylic acids and/or carboxylic acid esters and/or carboxylic acid anhydrides with the dialkanol amine to form a reaction mixture which contains N-acyl dialkanol amine and O-acyl dialkanol amine and a by-product derived from the used carboxylic acid derivative (water, alcohol). This by-product is removed from the reaction mixture using methods known in the art, such as, the use of a water separation funnel. This mixture is further reacted to effect cyclization to form the bicyclic amide acetal of the invention along with water as by-product. These two reaction steps can be carried out in the same reaction vessel without separation of process intermediates. For example, a carboxylic acid may react with dialkanol amine to form a bicyclic amide acetal.

The process of the present invention can be carried out, for example, by charging a suitable vessel, such as, a reactor, with the carboxylic acids and/or carboxylic acid esters and/or carboxylic acid anhydrides, the dialkanol amine and optionally, a solvent, to form the reaction mixture. Preferably, the reaction mixture is agitated, for example, by stirring or shaking.

The present bicyclic amide acetal derivatives can be individually isolated from the reaction mixture, using known conventional methods, such as, chromatography or fractional distillation or crystallization; the preferred method is distillation.

The process of this invention can be carried out with or without a solvent. The solvent, if used, can be liquid at the reaction temperature and pressure and inert towards the substrates and products of the process. Examples of suitable solvents include hydrocarbons, such as, benzene, xylene, decaline or combinations thereof; or combinations of two or more thereof. The charged reagents can themselves serve as the solvent.

During removal of the first equivalent of water to form the N-acyl or O-acyl dialkanol amines the pressure range is about 13,000 to 150,000 Pa, preferably 27,000 to 110,000 Pa. The subsequent dehydration step is run at a pressure of about 13 to 101,325 Pa, preferably 133 to 1333 Pa. The processing temperatures may be from 80 to 250° C. and preferably from 140-230° C.

The process may be carried out in batch, sequential batch (i.e., a series of batch reactors) or in continuous mode in any of the equipment customarily employed for continuous processes.

Alternatively, based on strategy B, the bicyclic amide acetals can be prepared directly according to the invention by dehydration of N-acyl dialkanol amines, i.e., starting with an intermediate product contained in the reaction mixture of the reaction described above. The N-acyl dialkanol amines can be prepared as known in the art (see for example J. of the American Oil Chemists' Society, 1962, 39, 213-15). Certain N-acyl dialkanol amines are commercially available (for example, Naxamide®-CD140 from Rütgers Organics) and/or can be prepared through alternative routes, for example in the reaction of carboxylic acid chlorides with the dialkanol amine. These N-acyl dialkanol amines can be dehydrated using the process of this invention to bicyclic amide acetals.

The process of the present invention can be carried out, for example, by charging a suitable vessel, such as a reactor, with the N-acyl dialkanol amines and optionally a solvent, to form the reaction mixture. Preferably, the reaction mixture is agitated, for example, by stirring or shaking. The pressure range for the reaction is about 13 Pa to 101325 Pa, and preferably, 133 to 1333 Pa. The processing temperatures may be from 80 to 250° C., preferably, 140 to 230° C. The process may be carried out in batch, sequential batch (i.e., a series of batch reactors) or in continuous mode in any of the equipment customarily employed for continuous processes.

The bicyclic amide acetals can also be prepared by reacting carboxylic amides with oxiranes to form reaction mixtures containing N-acyl alkanol amines and/or N-acyl dialkanol amines and which may contain oxazolines. These reaction mixtures can be dehydrated to generate the bicyclic amide acetals of this invention. Typical carboxylic amides are lauramide, acetamide, caproic amide, valeric amide. Typical oxiranes useful in this invention can be substituted with linear or branched alkyl, cycloalkyl or aryl groups; oxiranes based on glycidyl ethers are also substrates. Typical oxiranes include, ethyleneoxide, propyleneoxide, butyleneoxide, phenyl glycidyl ether, and butylglycidyl ether. The process can be carried out, for example, by charging a suitable vessel, such as a reactor, with the carboxylic amide and the oxirane in a ratio of 1 to 10, with a preferred ratio of 1 to 2.5 and optionally, a solvent to form the reaction mixture. Preferably, the reaction mixture is agitated, for example, by stirring or shaking. The pressure range for the reaction is 6666 to 202650 Pa, preferably 40000 to 101325 Pa. The processing temperatures may be from 80 to 250° C., preferably 140 to 230° C. The process may be carried out in batch, sequential batch (i.e. a series of batch reactors) or in continuous mode in any of the equipment customarily employed for continuous processes.

For each strategy, the use of water scavengers is optional in the process of the invention and can aid in the removal of the by-product water. The presence of a water scavenger can improve the process regarding speed of reaction, conversion and reaction temperature. Suitable water scavengers are, for example, orthoesters, orthoformates, orthoketals, orthocarbonates, alkoxysilanes and inorganic compounds e.g., $Na_2SO_4$, MgO, CaO, P2O5, molecular sieves. Alternatively, common methods applied to separate water from such reaction mixtures can also be used (for example, a water separation device such as a Dean Stark Trap).

The process of the present invention may be carried out in the presence of a catalyst. Examples of suitable catalysts include, metal oxides, hydroxides, carbonates, silicates, phosphates, aluminates, tertiary amines, pyridine and pyridine derivatives and combinations thereof. Suitable catalysts are also, for example, salts of metals, wherein the metal is selected from the group consisting of scandium, titanium, vanadium, chromium, manganese, iron, cobalt, nickel, copper, zinc, and cadmium.

The bicyclic amide acetals prepared according to the present invention can be used as latent hydroxyl compounds in coating compositions comprising compounds reactive with hydroxyl groups or amine groups, such as, polyisocyanates, epoxy-functional compounds, acetals, anhydrides and alkoxysilanes. The bicyclic amide acetals are stable under anhydrous conditions and hydrolyze in the presence of moisture, e.g., in the presence of atmospheric moisture, under formation of free hydroxyl groups or amine groups. The hydrolysis occurs without a catalyst, but the speed of hydrolysis can be increased by the addition of catalysts. Suitable catalysts are acids, e.g., acetic acid and sulfonic acids, such as p-toluenesulfonic acid.

Coating compositions based on bicyclic amide acetals dry and cure rapidly without the potential problems created by VOC (Volatile Organic Content) emissions. The coating compositions based on bicyclic amide acetals may comprise further hydroxy-functional binders, which are able to react with the crosslinkers mentioned above. Such coating compositions can be very useful, for example, in automotive coating, particularly, in the refinish area. They can be used as clear coats or pigmented coating compositions, e.g., solid-color top coats or primers.

A "clear coating composition" for automotive use is a composition that forms a transparent finish upon curing and has a DOI (distinctness of image) of more than 70 and a 20° gloss of more than 70. These clear coatings provide a glossy in depth appearance to the finish on the automobile or truck and therefore, are required to have good gloss and distinctness of image. Also, the clear finish provides resistance to weathering, in particular to U.V. degradation and photo-oxidation.

Coating compositions based on bicyclic amide acetals prepared according to the present invention show a better initial color and a better color stability than coating compositions based on bicyclic amide acetals prepared according to known methods. Especially, the color stability during storage of the bicyclic amide acetal prepared according to the invention (in the pure form as well as in a formulation with typical solvents) is improved compared with amide acetals prepared, e.g., via the nitrile route. Coating compositions based on bicyclic amide acetals prepared according to the present invention also have a long potlife and a high initial hardness. Coating compositions can be formulated with a low VOC of, e.g., 1.6 lbs/gal (192 g/l).

Having generally described this invention, a further understanding can be obtained by reference to certain specific examples, which are provided herein for purpose of illustration only and are not intended to be limiting.

EXAMPLES

Example 1

Preparation of 2,6-dimethyl-7a-undecyl-tetrahydro-2H-oxazolo[2,3-b]oxazole. To a 1 liter stirred reactor, equipped with a distillation column, condenser, and graduated receiver, the following constituents were added: 164.9 g of diisopropanol amine (DIPA, ChemCentral, Milwaukee, New Berlin, Wis.) and 201.5 g (98%) of lauric acid (Aldrich Chemical Co., Milwaukee, Wis.). The contents were heated to 180° C. under a nitrogen blanket. After 80 minutes, 17 ml of water had come overhead (1 equivalent). The batch temperature was held at 180° C. while the pressure was dropped to 320 Pa. The batch temperature was then raised to 195° C. During the pressure reduction and heat-up, unreacted DIPA (60 g) came overhead. A total of 199.4 g of amide acetal derived from lauric acid was then collected while the temperature was raised from 195 to 222° C. at a pressure of 320-466 Pa. This represents a 66.7% conversion of the lauric acid. Gas chromatography (GC) was used for the determination of diisopropanol amine (DIPA) and amide acetal content in the liquid samples. Liquid samples from the reactor and from the overhead receiver were analyzed for the presence of DIPA and amide acetal product using an internal standard GC method. The GC was calibrated using pure DIPA and amide acetal. Samples were removed, weighed, diluted with known amount of internal standard in methylene chloride, and then injected into the GC.

Example 2

Preparation of 2,6-dimethyl-7a-undecyl-tetrahydro-2H-oxazolo[2,3-b]oxazole. To a 5 liter stirred reactor, equipped with a distillation column, condenser, and graduated receiver, the following constituents were added: 1250.0 g of diisopropanol amine (DIPA) and 1502.5 g (98%) of lauric acid. The contents were heated to 186° C. under a nitrogen blanket over a 90 minute period. During that time, 136 ml of water came overhead. The batch temperature was held at 184° C. while the pressure was dropped to 320 Pa. During the pressure reduction, 410 g of unreacted DIPA came overhead. A total of 1192 g of amide acetal derived from lauric acid was collected while the temperature was raised to 220° C. at a pressure of 280-466 Pa. This represents a 53.5% conversion of the lauric acid.

Example 3

Preparation of 2,6-dimethyl-7a-undecyl-tetrahydro-2H-oxazolo[2,3-b]oxazole. To a 1 liter stirred reactor, equipped with a distillation column, condenser, and graduated receiver, the following constituents were added: 166.5 g of diisopropanol amine (DIPA) and 200.0 9 (98%) of lauric acid. The contents were heated to 186° C. under a nitrogen blanket. After 111 minutes, 15 ml of water had come overhead. The batch temperature was allowed to drop to 172° C. while the pressure was dropped to 10,531 Pa. The batch temperature was then raised to 195° C. and the pressure was raised to 13,330 Pa. The batch temperature was slowly raised to 220° C. while the batch pressure was increased to 19,800 Pa. An additional 13 ml of a mixture of water and DIPA came overhead. The temperature was then allowed to drop to 182° C. while the pressure was dropped to 280 Pa. During the pressure reduction, 31.2 g of DIPA came overhead. As the pressure was dropped to 227 Pa and the temperature increased to 221° C., a total of 93.4 g of the amide acetal of lauric acid was collected.

Example 4

Preparation of the amide acetal of adipic acid. To a round bottom flask with a Dean Stark trap and a condenser under atmospheric nitrogen, the following constituents were added: 27.34 g of diisopropanolamine and 15 g adipic acid (in a ratio of 2:1 mol). The resulting mixture was stirred and heated to 200° C. The formation of water was observed (about 2 equivalents). The reaction was held at 200° C. and placed under a vacuum of 40 Pa. During this time, remaining unreacted DIPA and newly formed water were distilled into the Dean Stark trap. The reaction mixture solidified upon cooling. NMR analysis of the reaction mixture revealed the formation of amide acetal and unreacted amide-ester fractions.

Example 5

Preparation of 7a-butyl-2-hexyl-6-methyl-tetrahydro-2H-oxazolo[2,3-b]oxazole. Under atmospheric nitrogen, 30.79 g of 1-amino-2-propanol was added drop-wise to a solution of 52.59 g of 1,2-epoxyoctane (in a ratio of 1:1 mol) in acetonitrile (100 g). The mixture was stirred and eventually solidified followed by the removal of acetonitrile in vacuum. Under atmospheric nitrogen, 30.00 g of valeric acid and the product of the first step, 83.33 g of 2-(2-hydroxypropylamino)octan-1-ol (in a ratio of 1:1.5 mol) were added to a flask with a Dean Stark trap and a condenser. The reaction mixture was heated to 180° C. and stirred. Water was collected in the trap. The reaction flask was connected to a distillation apparatus. At 180° C. and under a vacuum of 1.33 Pa, approximately 30 g were distilled over to a flask containing molecular sieves to absorb the final equivalent of water. The product was distilled from the reaction mixture and further purified by extraction with petroleum ether followed by distillation. The product, 7a-butyl-2-hexyl-6-methyl-tetrahydro-2H-oxazolo[2,3-b]oxazole, was isolated with 20% yield.

Example 6

Preparation of 7a-(2-(2,6-dimethyl-tetrahydro-2H-oxazolo[2,3-b]oxazol-7a-yl)ethyl)-2,6-dimethyl-tetrahydro-2H-oxazolo[2,3-b]oxazole. To a round bottom flask with a Dean Stark trap and a condenser under atmospheric nitrogen, the following constituents were added: 7.99 g of diisopropanolamine and 3 g of succinic anhydride (in a ratio of 2:1 mol). The reaction mixture was heated to 200° C. with mixing. Water was collected in the trap. The reaction mixture at 200° C. was then put under a vacuum of 4.0 Pa to remove any additional amounts of water. The formation of amide acetal was confirmed in the reaction mixture using NMR spectroscopy. A conversion of 37% was observed while the remaining material was a mixture of amide and ester products.

Example 7

Preparation of 7a-butyl-2,6-pentyl-tetrahydro-2H-oxazolo[2,3-b]oxazole. To a round bottom flask with a Dean Stark trap and a condenser under atmospheric nitrogen, the following constituents were added: valeramide and 1,2-epoxyoctane (in a ratio of 1:2 mol). Di-methyl-aminopyridine was added as a catalyst. The reaction mixture was heated to 80° C. with mixing. The reaction temperature was raised to 180° C. and was then put under a vacuum of about 4.0 Pa to remove any water. The formation of amide acetal was confirmed in the reaction mixture using NMR spectroscopy.

Example 8

Preparation of 2,6-dimethyl-7a-(6-methylheptyl)-tetrahydro-2H-oxazolo[2,3-b]oxazole. To a 1 liter stirred reactor, equipped with a distillation column, condenser, and graduated receiver, the following constituents were added: 331.2 g of diisopropanol amine (DIPA) and 390.5 g (98%) of isononanoic acid. The contents were heated to 180° C. under a nitrogen blanket. After 3.5 hours, 43.4 g of water was collected overhead. The pressure was then slowly lowered to strip out unreacted DIPA. At a batch temperature of 183° C. and a pressure of 60 Pa, a cut consisting of 188 g of DIPA was removed. The batch temperature was then raised to 200° C. and the pressure dropped 333 Pa. During this period, a cut of 220 g of the amide acetal was recovered. The water of reaction passed through the condenser and was not captured with the amide acetal. This represents a 35% conversion of the isononanoic acid to amide acetal.

Example 9

Preparation of 2,6-dimethyl-7a-undecyl-tetrahydro-2H-oxazolo[2,3-b]oxazole. To a 1 liter stirred reactor, equipped with a distillation column, condenser, and graduated receiver, the following constituents were added: 261.2 g of diisopropanol amine (DIPA) and 432.0 g (98%) of methyl laurate. The contents were heated slowly to 230° C. under a nitrogen blanket. After 5.5 hours, 57 ml of methanol (0.72 equivalent) had come overhead. The pressure was then slowly lowered to strip out unreacted DIPA. At a batch temperature of 180° C. and a pressure of 293 Pa, a cut consisting of 79.7 g of DIPA and 87.8 g of methyl laurate was removed. The batch temperature was then raised to 200° C. and the pressure dropped to 267 Pa. During this period, a cut of 140.9 g of the amide acetal was recovered. This represents a 35.7% conversion of the methyl laurate to amide acetal.

Example 10

Preparation of 2,6-dimethyl-7a-undecyl-tetrahydro-2H-oxazolo[2,3-b]oxazole. In a first stage to a reactor, equipped with a distillation column, condenser, and graduated receiver, 199.8 g (1.5 mol) of diisopropanol amine (DIPA) and 7.5 g of $CH_3ONa$ (30% in methanol) were added and the batch heated to 75° C. 160.5 g (0.75 mol) of methyl laurate were added during 2 hours at 75° C. Temperature was gradually increased during 3 hours. Methanol has been removed at lower pressure 26,660 Pa) and at 120° C. and excess of DIPA has been removed at a pressure below 133 Pa and at 140° C. The so prepared amide looked as yellow fat (melting temperature of above 130° C). In a second stage 0.5 weight % of zinc acetate, based on the intermediate product after stage 1 were added and the batch was heated at 180° C. for 6 hours. Fraction distillation has been done at a pressure below 133 Pa. Three fractions were obtained: I) with boiling point <105° C.; amount above 5 weight %; mainly DIPA; II) with boiling point 105-145° C.; amount 50 weight %; amide acetal (purity 90%) and III) 45 weight %—distillation rest. The yield of amide acetal calculated on methyl laurate was 43%. Initial color and color stability during storage (on shelf) of an amide acetal prepared according to the invention and a comparative amide acetal prepared from nitriles have been evaluated. The amide acetal according to the invention shows a better initial color and better color stability than the amide acetal prepared from nitrites.

|  | Initial* | 1 month* | 2 months* | 3 months* |
|---|---|---|---|---|
| Amide acetal of example 1 | 10 | 10 | 10 | 10 |
| Comparative Amide Acetal (1) | 30 | 30 | 30 | 30 |
| Comparative Amide Acetal (2) | 15 | 25 | 30 | 30 |

*Hazen Color
(1) The comparative amide acetal has been prepared by reacting dodecane nitrile and diisopropanol amine.
(2) The comparative amide acetal has been prepared by reacting dodecane nitrile and diisopropanol amine (with Na catalyst).

Preparation of Clearcoats

Clear coat formulations (CC A and CC B) based on amide acetals have been prepared by mixing the following constituents, whereas CC A is based on amide acetal of example 1 according to the invention and CC B is based on comparative amide acetal (1):

| Part 1 | A | B |
|---|---|---|
| amide acetal of example 1 | 36.09 | |
| comparative amide acetal (1) | | 36.09 |
| 10% DBTDL (dibutyltin dilaurate) in xylene | 2.62 | 2.62 |
| Byk 358 (acrylic leveling agent from Byk Chemie) | 0.2 | 0.2 |
| Byk 310 (silicon surface additive from Byk Chemie) | 0.2 | 0.2 |
| diisobutylketone | 5.05 | 5.05 |
| acetic acid | 0.58 | 0.58 |

Two activator solutions (AA and AB) were prepared by blending 34.27 parts of (1) and 20.99 parts of (2)

| Part 2 | AA | AB |
|---|---|---|
| (1) Desmodur ® N3600, Bayer (100% solids, HDI (hexamethylene diisocyanate) trimer) | 34.7 | 34.27 |
| (2) Vestanat ® T1890L, Degussa (70% solids in BuAc/Solvesso) BuAc (butylacetate) Solvesso (hydrocarbon-solvent) | 20.99 | 20.99 |

A usual two-component high solid clearcoat (based on hydroxy functional acrylic binder and polyisocyanate activator) has been used as solventborne comparative clear coat (comparative CC; 3800S HS Chromaclear® (DuPont)+high solid activator XK205 (DuPont)).

Clearcoat: 47.36% solids
Activator: 70.44% solids

| XK205 High Solid Activator | |
|---|---|
| 10.22 | BuAc |
| 11.205 | xylene |
| 0.343 | 10% DBTDL in BuAc "(dibutyltin dilaurate) |
| 78.23 | Desmodur ® N3390 (HDI Trimer (90% solids in BuAc/Solvesso 100) Bayer) |

Activation:

3:1 activation ratio of 3800S:XK205 by weight: 100 g 3800S:36.6 g XK2205

| Determination of Initial Color and Color After Storage of Clearcoats | | |
|---|---|---|
|  | CC A | CC B |
| initial color* of amide acetal | 10 | 30 |
| color* after 2 weeks oven storage (49° C.) | 15 | 35 |
| color* after 4 weeks oven storage (49° C.) | 15 | 40 |

*Hazen color

|  | CC A | CC B | Comparative CC |
|---|---|---|---|
| Solids | 81.70% | 81.70% | 53.60% |
| NCO/OH | 1.15 | 1.15 | 1.18 |
| theoretical VOC (lbs/gal) | 1.6 | 1.6 | 3.8 |
| spray viscosity (seconds)* | 24 | 24 | 18 |
| potlife** | >6 hours | >6 hours | 1.5 hours |

*measured according to DIN EN ISO 2431 with 4 mm cup
**time within which initial viscosity increases to initial viscosity x 1.5

The clearcoats have been applied over usual solventborne basecoats (Centari 6000 silver metallic basecoat) and cured 30 minutes at 60° C.

The results are given in the table below:

|  | CC A | CC B | Comparative CC |
|---|---|---|---|
| number of coats (with HVLP spray gun) | 1 | 1 | 1.5 |
| dry film thickness (μm) | 50 | 50 | 55 |
| tack free time (minutes) | imm*. | imm*. | 8 |
| tape free time (hours) | 3 | 3 | 92 |
| DOI | 87 | 88 | 84 |
| Long wave | 3.1 | 2.6 | 3.2 |
| Short wave | 10.2 | 10.8 | 14.6 |

*= immediately

The clear coat based on the amide acetal prepared according to the present invention (CC A) shows the advantage of a very low VOC value (1.6 lbs/gal) compared with a usual high solid clearcoat at a comparable spray viscosity. Furthermore said clearcoat gives an improved potlife of more than 6 hours. The clearcoat is still easy to spray 6 hours after activation and the drying-appearance (gloss, DOI) is still the same like for the composition that is sprayed directly after activation.

The amide acetals prepared according to the present invention show less color and a better color stability compared with the amide acetal prepared according to the prior art process (via nitrile route). Color and color stability are important issues especially in formulating high-quality clearcoats.

Test Methods

Tack Free Time

A film is considered to have dried tack-free when the tack tester tips over immediately on removing a 300 g weight allowed to act for 5 seconds on the counter-weighted metal square based fitted with masking tape and aluminum foil. (Technical data for tack tester according to ASTM D1640 page 273)

Tape Free Time:
applying a strip of masking type across the panel
smoothing it out with the finder using moderately firm pressure to insure uniform contact
rolling over the tape with 2 kg weight to an from
removing the tape after 10 minutes and observing the degree of
marking
waiting 30 minutes and checking again the film for tape imprint.

Possible ratings are: very, very poor; very poor; poor; fair; good; very good; excellent "Tape free time" is the time after which the recovery has the rating "good". The recovery is the re-evaluation that is done 30 minutes after the tape is removed. When the tape recovery has a rating good, there is almost no mark left. A rating good means also commercially acceptable.

What is claimed is:

1. A process for preparing amide acetals represented in Formula I comprising dehydrating a reactant mixture comprising reactants selected from a group consisting of N-acyl dialkanol amines, O-acyl dialkanol amines and mixtures thereof

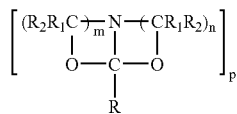

Formula I wherein
n and m are independently selected from the group of 2 or 3; p is 1, 2 or 3; R1 and R2 can be the same or different and are each independently selected from the group of hydrogen, a linear or branched alkyl, cycloalkyl or aryl group with 1-20 C atoms; R represents hydrogen, a branched or linear alkyl, cycloalkyl, aryl or an alkenyl group with 1-20 C-atoms, each may have one or more substituents.

2. The process according to claim 1, wherein the reactant mixture comprising reactants selected from a group consisting of N-acyl dialkanol amines, O-acyl dialkanol amines and mixtures therefrom is prepared by reacting at least one carboxylic acid and/or carboxylic acid ester and/or carboxylic acid anhydride and at least one dialkanol amine.

3. The process according to claim 2, wherein this process is combined directly with the dehydration process to form the bicyclic amide acetals of Formula I.

4. The process according to claim 2, wherein the dialkanolamine is selected from a group consisting of diethanol amine, diisopropanol amine, di-n-propanol amine or mixtures thereof.

5. The process according to claim 2, wherein the carboxylic acid is selected from a group consisting of lauric acid, isononanoic acid and mixtures thereof.

6. The process according to claim 1, wherein the temperature of the dehydrating reaction is in the range of 80° C. to 250° C. and the pressure of the dehydrating reaction is in the range of 13 to 101,325 Pa.

7. The process according to claim 1, wherein the temperature of the dehydrating reaction is in the range of 140° C. to 230° C. and the pressure of the dehydrating reaction is in the range of 133 to 1333 Pa.

8. The process according to claim 2, wherein the temperature of the reaction of the at least one carboxylic acid and/or carboxylic acid ester and/or carboxylic acid anhydride with the at least one dialkanol amine is in the range of 80° C. to 250° C. and the pressure in the range of 13,000 to 150,000 Pa.

9. The process according to claim 2, wherein the temperature of the reaction of the at least one carboxylic acid and/or carboxylic acid ester and/or carboxylic acid anhydride with the at least one dialkanol amine is in the range of 140° C. to 230° C. and the pressure in the range of 27,000 to 110,000 Pa.

* * * * *